United States Patent
Schon et al.

(10) Patent No.: US 8,978,688 B2
(45) Date of Patent: Mar. 17, 2015

(54) DUAL MODE ELECTRONIC FLOW CONTROL SYSTEM

(71) Applicant: Mindray DS USA, Inc., Mahwah, NJ (US)

(72) Inventors: Peter B. Schon, New York, NY (US); Christine M. Manfredo, S. Plainfield, NJ (US); Li Xinsheng, Shenzhen (CN); Huang Chenghua, Shenzhen (CN); Zhu Guanyu, Shenzhen (CN)

(73) Assignee: Shenzhen Mindray Bio-Medical Electronics Co. Ltd., Shenzhen (CN)

(*) Notice: Subject to any disclaimer, the term of this patent is extended or adjusted under 35 U.S.C. 154(b) by 83 days.

(21) Appl. No.: 13/677,157

(22) Filed: Nov. 14, 2012

(65) Prior Publication Data

US 2014/0130905 A1    May 15, 2014

(51) Int. Cl.
  *G05D 11/00*    (2006.01)
  *G05D 7/06*    (2006.01)

(52) U.S. Cl.
  CPC .................................. *G05D 7/0617* (2013.01)
  USPC . 137/101.19; 137/606; 137/607; 251/129.01; 128/203.12; 128/204.18

(58) Field of Classification Search
  CPC ..... A61M 16/18; A61M 16/12; A61M 16/20; A61M 2202/0283; A61M 2205/16; A61M 2205/17; A61M 2205/103; A61M 2205/106; A61M 2205/502; A61M 2205/505; A61M 2205/3334; A61M 2205/3341

USPC .............. 137/606, 625.31, 101.19, 602, 889, 137/896, 897, 607, 898; 128/203.12, 128/203.13, 203.14, 203.16, 203.17, 128/204.18, 204.21; 251/129.01, 129.04, 251/129.08
  See application file for complete search history.

(56) References Cited

U.S. PATENT DOCUMENTS

| | | | |
|---|---|---|---|
| 6,857,443 B2 * | 2/2005 | Volgyesi ................... | 137/101.19 |
| 7,624,757 B2 * | 12/2009 | Schmitt ......................... | 137/606 |
| 7,836,882 B1 * | 11/2010 | Rumph et al. ........... | 128/203.12 |
| 2006/0196505 A1 * | 9/2006 | Izuchukwu ............... | 128/203.15 |
| 2008/0108884 A1 * | 5/2008 | Kiani ............................ | 600/301 |
| 2010/0095961 A1 * | 4/2010 | Tornesel et al. .......... | 128/203.12 |
| 2010/0175695 A1 * | 7/2010 | Jamison ................... | 128/203.14 |
| 2012/0318263 A1 * | 12/2012 | Jones et al. ............. | 128/203.12 |
| 2012/0318264 A1 * | 12/2012 | Jones et al. ............. | 128/203.14 |
| 2012/0325208 A1 * | 12/2012 | Heesch .................... | 128/203.25 |
| 2013/0019867 A1 * | 1/2013 | Mashak ................... | 128/203.12 |

* cited by examiner

*Primary Examiner* — Matthew W Jellett
(74) *Attorney, Agent, or Firm* — Kory D. Christensen; Stoel Rives LLP (57) ABSTRACT

In various embodiments, two or more electronic flow selectors of an electronic fluid flow control system may be used to control the flow rates of multiple fluids. In a total flow control mode, a first electronic flow selector may be used to select a total flow rate of two or more fluids. A second electronic flow selector may be used to select a flow rate or ratio of a flow rate of one fluid to the total flow rate of the two or more fluids. In a direct flow control mode, each electronic flow selector may be used to select a flow rate of a unique fluid. One of the fluids may be oxygen, and the other fluid, a balance gas, may be selected as either nitrous oxide or air using an electronic balance gas selector.

31 Claims, 8 Drawing Sheets

DUAL MODE ELECTRONIC FLOW CONTROL SYSTEM

TECHNICAL FIELD

This disclosure relates generally to controlling the flow of fluids via electronic controls. Particularly, this disclosure relates to electronic flow selectors configured to operate in multiple selectable modes while maintaining physical similarity to manual flow selectors.

SUMMARY

In various instances, the flow rates of fresh gases, such as oxygen, nitrous oxide, and air, in modern anesthesia delivery systems may be controlled by a practitioner either electronically or mechanically. In various embodiments, one or more rotatable flow selectors, such as rotatable knobs, may be configured to electronically control a flow rate of a gas when in a powered state. The anesthesia delivery system may also include manual backup controls for controlling the flow rate of one or more of the gases when in an unpowered state. In one embodiment, a three-way selector valve and/or a combination of normally-open valves and normally-closed valves may be used to selectively enable the flow of gas from either electronically controlled electronic proportional valves or mechanically operated needle valves. The valve assemblies, flow selectors, and position detection systems may be utilized with or without variation in any of a wide variety of flow control systems.

In various embodiments, when a fluid flow control system is in a powered state, a three-way selector valve, or other diversion valve system, may allow fluid from the electronically controlled electronic proportional valves to be delivered to a patient. When the fluid flow control system is in an unpowered state or a manual override is selected, the three-way selector valve may allow fluid from the mechanically controlled needle valves to be delivered to a patient. Alternatively, a diversion valve system may include a combination of normally-open and normally-closed valves instead of or in addition to a three-way selector valve, as described herein. In some embodiments, the diversion valve system may be located between a fluid supply and a fluid control valve. In other embodiments, the diversion valve system may be located between a fluid control valve and a fluid output.

An electronic flow control valve, such as an electronically controlled proportional valve, may be configured to selectively receive a fluid from a fluid supply. An electronic flow selector may allow a practitioner to select a flow rate of the first fluid via the electronic control valve. From the perspective of the user, the electronic flow selector may be functionally similar to a control knob for a mechanical needle valve. For example, a user may rotate a knob clockwise or counter-clockwise in order to decrease or increase, respectively, the flow rate of a particular fluid. A rotary encoder may electronically encode a selection made via the electronic flow selector and transmit the encoded selection to an electronic controller. The electronic controller may transmit a control signal to the electronic flow control valve to control the flow rate of the fluid based on the selection made via the electronic flow selector.

As described in the example, the electronic flow control valve may include an electronic proportional valve and the electronic flow selector may include a rotary knob configured to be manually rotated by a user. Alternatively, the electronic flow selector may include any of a wide variety of digital and/or analog selectors with accompanying encoders. For example, a slider may be adjusted between a zero flow rate point and a 100 percent flow rate point. A sliding encoder may electronically encode the selection made via the slider.

In some embodiments, one or more unique electronic flow control valves may be used to control the flow rate of each available fluid. For example, a first electronic flow control valve may control the flow rate of oxygen. A second electronic flow control valve may control the flow rate of nitrous oxide. A third electronic flow control valve may control the flow rate of air. A fourth electronic flow control valve may control the flow rate of a fourth gas.

Similarly, a unique electronic flow selector may be available to control the flow rate of each of the electronic flow control valves. Alternatively, one or more of the electronic flow selectors may be selectively assignable to control two or more electronic flow control valves. For example, a system may include three electronic flow control valves, one for oxygen, one for air, and one for nitrous oxide. The system may utilize only two electronic flow selectors, one of which may be selectively used to control either the flow rate of the air or the flow rate of the nitrous oxide, and the other assigned to control the flow rate of oxygen. Any electronic flow selector may be permanently assigned or selectively assigned to control the flow rate of any one or more of the available fluids.

In some embodiments, the system may utilize two electronic flow selectors to selectively control the flow rate of oxygen and nitrous oxide, or oxygen and air. The flow selectors may be utilized in a direct flow mode in which a first electronic flow selector is used to directly adjust the flow rate of oxygen and a second electronic flow selector is used to directly adjust the flow rate of either nitrous oxide or air. A digital display associated with the selected flow rates may display the selected flow rates of each gas, a total flow rate, the ratio of the two gases, the total flow rate with respect to an optimum flow rate, and/or other numeric values, charts, graphs, percentages, and the like.

The flow selectors may additionally, selectively, or alternatively be used in a total flow mode in which a first electronic flow selector is used to adjust the total flow rate of the selected balance gas (air or nitrous oxide) and oxygen delivered and a second electronic flow selector is used to control the concentration of oxygen to mix with the selected balance gas (air or nitrous oxide). The ratio may be computed and graphically represented in digital or mechanically operated flow tubes (e.g., variable area flowmeters). The digital display may display a numeric value associated with the delivery flow rate of each individual gas (e.g., in liters per minute). In various embodiments, the digital display may display the total flow rate, the ratio of the two gases, the total flow rate with respect to an optimum flow rate, and/or other numeric values, charts, graphs, percentages, and the like associated with the flow rates.

In addition to electronic control valves, one or more mechanical flow control valves may be configured to control the flow rate of each of the available fluids. For example, a unique needle valve may be used to mechanically control the flow rate of each available fluid. A manual flow selector, such as a knob or slider, may be actuated by a practitioner to mechanically adjust the flow rate through each of the needle valves. In some embodiments, the manual flow selectors may be disabled and/or retracted to prevent adjustments when the system is in a powered state.

In a powered state, one or more electronic flow selectors may be adjusted to control the flow rate of one or more fluids through one or more electronic flow control valves. In the powered state, backup mechanical flow control valves may be disabled and/or otherwise prevented from supplying a fluid or combination of fluids. Moreover, in the powered state, manual flow selectors associated with the backup mechanical flow control valves may be disabled and/or retracted to prevent adjustments.

In an unpowered state, or when a manual override selection is made, the electronic flow control valves may be disabled and/or otherwise prevented from supplying a fluid or combination of fluids. Manual flow selectors may be enabled and/or deployed to allow a practitioner to directly control a flow rate of one or more fluids through the backup mechanical flow control valves.

In some embodiments, when the manual flow selectors are retracted, such as upon power restoration or a reset of the system, the flow rate of each of the backup mechanical flow control valves may be reset to a home state, in which a predetermined flow rate of a gas will automatically flow when the system enters an unpowered state.

In one embodiment, the electronic flow control valve may comprise an electronically controlled stepper motor configured to adjust the flow rate of a fluid through a mechanical flow control valve, such as a needle valve. In various examples provided herein, the fluid is described as a gas, such as oxygen, nitrous oxide, and/or air. However, any of a wide variety of liquids and/or gases may be used in conjunction with various embodiments of the systems and methods described herein.

DETAILED DESCRIPTION

An electronic flow control valve, such as an electronically controlled proportional valve, may be configured to selectively receive a fluid from a fluid supply. An electronic flow selector may allow a practitioner to select a flow rate of the first fluid via the electronic control valve. From the perspective of the user, the electronic flow selector may be functionally similar to a control knob for a mechanical needle valve. For example, a user may rotate a knob clockwise or counter-clockwise in order to decrease or increase the flow rate of a particular fluid. A rotary encoder may electronically encode a selection made via the electronic flow selector and transmit the encoded selection to an electronic controller. The electronic controller may transmit a control signal to the electronic flow control valve to control the flow rate of the fluid based on the selection made via the electronic flow selector.

One or more of the electronic flow selectors may be selectively assignable to control two or more electronic flow control valves. For example, a system may include three electronic flow control valves, one for oxygen, one for air, and one for nitrous oxide. The system may utilize only two electronic flow selectors, one of which may be selectively used to control either the flow rate of the air or the flow rate of the nitrous oxide, and the other assigned to control the flow rate of oxygen. Any electronic flow selector may be permanently assigned or selectively assigned to control the flow rate of any one or more of the available fluids.

In some embodiments, the system may utilize two electronic flow selectors to selectively control the flow rate of oxygen and nitrous oxide, or oxygen and air. The flow selectors may be utilized in a direct flow mode in which a first electronic flow selector is used to directly adjust the flow rate of oxygen and a second electronic flow selector is used to directly adjust the flow rate of either nitrous oxide or air. A digital display associated with the selected flow rates may display the selected flow rates of each gas, a total flow rate, the ratio of the two gases, the total flow rate with respect to an optimum flow rate, and/or other numeric values, charts, graphs, percentages, and the like associated with the flow rates.

The flow selectors may additionally, selectively, or alternatively be used in a total flow mode in which a first electronic flow selector is used to adjust the total flow rate of the selected balance gas (air or nitrous oxide) and oxygen delivered and a second electronic flow selector is used to control the concentration of oxygen to mix with the selected balance gas (air or nitrous oxide). The ratio may be computed and graphically represented in digital or mechanically operated flow tubes (e.g., electronic displays resembling variable area flowmeters). The digital display may display a numeric value associated with the delivery flow rate of each individual gas (e.g., in liters per minute). In various embodiments, the digital display may display the total flow rate, the ratio of the two gases, the total flow rate with respect to an optimum flow rate, and/or other numeric values, charts, graphs, percentages, and the like associated with the flow rates.

While electronic flow control of gases may be useful during anesthesia delivery, it may be desirable to provide manual backup controls as well. For example, in the event of power loss, it may be desirable to continue supplying gases during anesthesia delivery. In some embodiments, electronic controls, such as trim knobs, used in conjunction with encoders, may facilitate the electronic adjustment of the flow rate of one or more gases during anesthesia delivery. Separate backup flow selectors (e.g., knobs) may be available for use in the event of power failure or power unavailability. In such embodiments, the practitioner may need to engage the backup knobs, switch the machine from an electronic mode to a manual mode, and/or ensure that the manual knobs are set to a desirable state prior to switching to a manual mode. In various embodiments, the manual knobs may automatically return to a home state when retracted, such that the flow rate of each of the nitrous oxide, air, and oxygen is automatically set to a default flow rate when the manual knobs are deployed.

Power loss during anesthesia delivery may be confusing and/or disruptive during a critical medical procedure. It may be an inconvenience and/or confusing for a practitioner to see two sets of knobs for controlling the same set of gases. In various embodiments of the present disclosure, flow selectors, such as rotary knobs, may be electronically operable when a fluid flow control system is in a powered state and backup flow selectors may be retracted or otherwise disabled when a fluid flow control system is in a powered state. Confusion may be minimized because the electronic selectors are functionally similar to the manual flow selectors. In an unpowered state, or when a practitioner engages the backup system, the backup flow selectors may be deployed or otherwise enabled.

The number of diversion valve systems, mechanically operated valves, electronically operated valves, controllers, encoders, flow selectors, and/or other components described herein may correspond to the number of gases (or liquids) available. In various anesthesia delivery systems, oxygen, nitrous oxide, and/or air may each be independently controllable and/or proportionally controllable. A mixture of one or more gases may be used in conjunction with a vaporizer to deliver anesthesia.

In one embodiment, a diversion valve system may direct the flow of a gas (or liquid) from a gas supply to either a mechanical flow control valve, such as a mechanically operated needle valve, or an electronic flow control valve, such as an electronic proportion valve, depending on whether the system has power or if a backup system has been engaged.

According to various embodiments, the diversion valve system may include normally-open and normally-closed valves in order to selectively prevent the gas from flowing from (or to) both the mechanically operated needle valve and the electronic proportion valve. The diversion valve system may be implemented using any of a wide variety of valves and/or control systems, such as a three-way selector valve.

In some embodiments, the needle valve may be used as the mechanical flow control valve and the same needle valve in combination with the electronic stepper motor may be considered the electronic flow control valve. In various embodiments, the flow selector may comprise any of a wide variety of knobs, buttons, rotatable actuators, slides, and/or other analog and/or digital selection devices.

In various embodiments, a controller or control system may be implemented as any combination of hardware, firmware, and/or software. For example, a controller may be implemented as a field-programmable gate array (FPGA). In some embodiments, an electronic controller for transmitting a control signal to an electronic flow control valve may be distinct from other electronic components in a gas flow control system, such as microprocessors and other electronic components associated with displays, touch screens, data storage, data connectivity, etc. The reliability of the electronic flow controls may be improved by separating the electronic flow controls from other electronic features of an anesthesia delivery device and/or by implementing them in hardware rather than software.

While the various examples and embodiments disclosed herein are described in conjunction with a gas flow control system, many of the embodiments could be used or modified for use with any type of fluid, including various gases and liquids. Gases used for anesthesia delivery, such as oxygen, nitrous oxide, and air, are used herein as examples of gases that can be controlled via the presently described fluid flow control systems and are referred to as gas flow control systems.

Some of the infrastructure that can be used with embodiments disclosed herein is already available, such as general-purpose computers, computer programming tools and techniques, digital storage media, and communication networks. A computing device or other electronic controller may include a processor, such as a microprocessor, a microcontroller, logic circuitry, and/or the like. The processor may include a special purpose processing device such as application-specific integrated circuits (ASIC), programmable array logic (PAL), programmable logic array (PLA), a programmable logic device (PLD), FPGA, or another customizable and/or programmable device. The computing device may also include a machine-readable storage device, such as non-volatile memory, static RAM, dynamic RAM, ROM, CD-ROM, disk, tape, magnetic, optical, flash memory, or another machine-readable storage medium. Various aspects of certain embodiments may be implemented using hardware, software, firmware, or a combination thereof.

The embodiments of the disclosure will be best understood by reference to the drawings, wherein like parts are designated by like numerals throughout. The components of the disclosed embodiments, as generally described and illustrated in the figures herein, could be arranged and designed in a wide variety of different configurations. Furthermore, the features, structures, and operations associated with one embodiment may be applicable to or combined with the features, structures, or operations described in conjunction with another embodiment. In other instances, well-known structures, materials, or operations are not shown or described in detail to avoid obscuring aspects of this disclosure.

Thus, the following detailed description of the embodiments of the systems and methods of the disclosure is not intended to limit the scope of the disclosure, as claimed, but is merely representative of possible embodiments. In addition, the steps of a method do not necessarily need to be executed in any specific order, or even sequentially, nor do the steps need to be executed only once.

Figure 1:
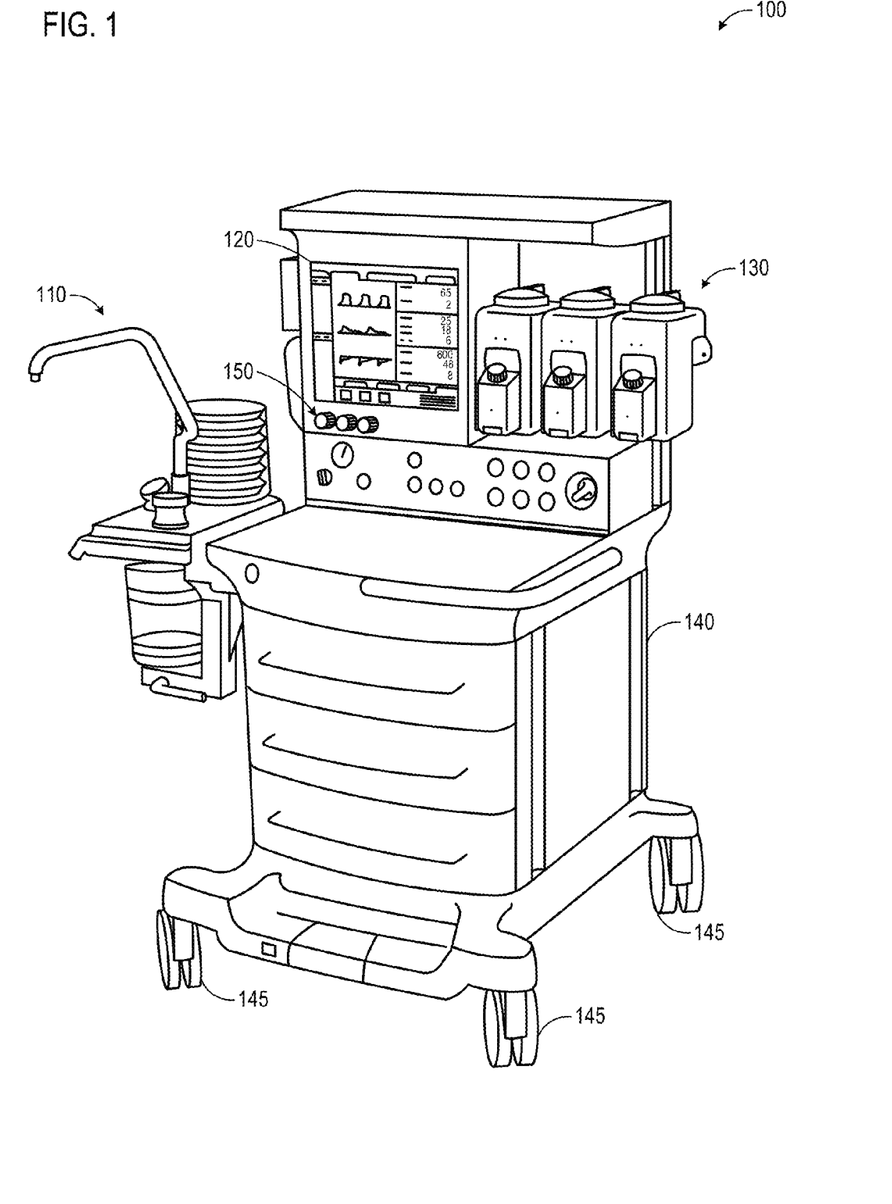
FIG. 1 illustrates an anesthesia delivery machine configured with three manual flow selectors, one each for controlling the flow of oxygen, nitrous oxide, and air.

FIG. 1 illustrates an anesthesia delivery machine 100 configured with three manual flow selectors 150, one each for controlling the flow of oxygen, nitrous oxide, and air. The illustrated anesthesia delivery machine 100 may include a breathing system 110, anesthetic gas vaporizers 130, and/or other components of an anesthetic delivery system. The anesthesia delivery machine 100 may include a cart 140 and/or wheels 145 for portability. An electronic display 120 may provide information regarding the flow rate and/or anesthetic delivery process to a practitioner. Additionally, the electronic display 120 may be configured as a touch sensitive display to allow a practitioner to provide inputs or selections associated with the displayed content.

In various embodiments, a user may rotate a manual flow selector 150 (e.g., a rotatable knob) clockwise or counter-clockwise in order to decrease or increase, respectively, the flow rate of a particular fluid (e.g., oxygen, nitrous oxide, air). In various embodiments, the number of manual flow selectors 150 may correspond to the number of available fluids for control. Accordingly, any number of manual flow selectors may be utilized based on the number of available gases (or other fluids).

Figure 2:
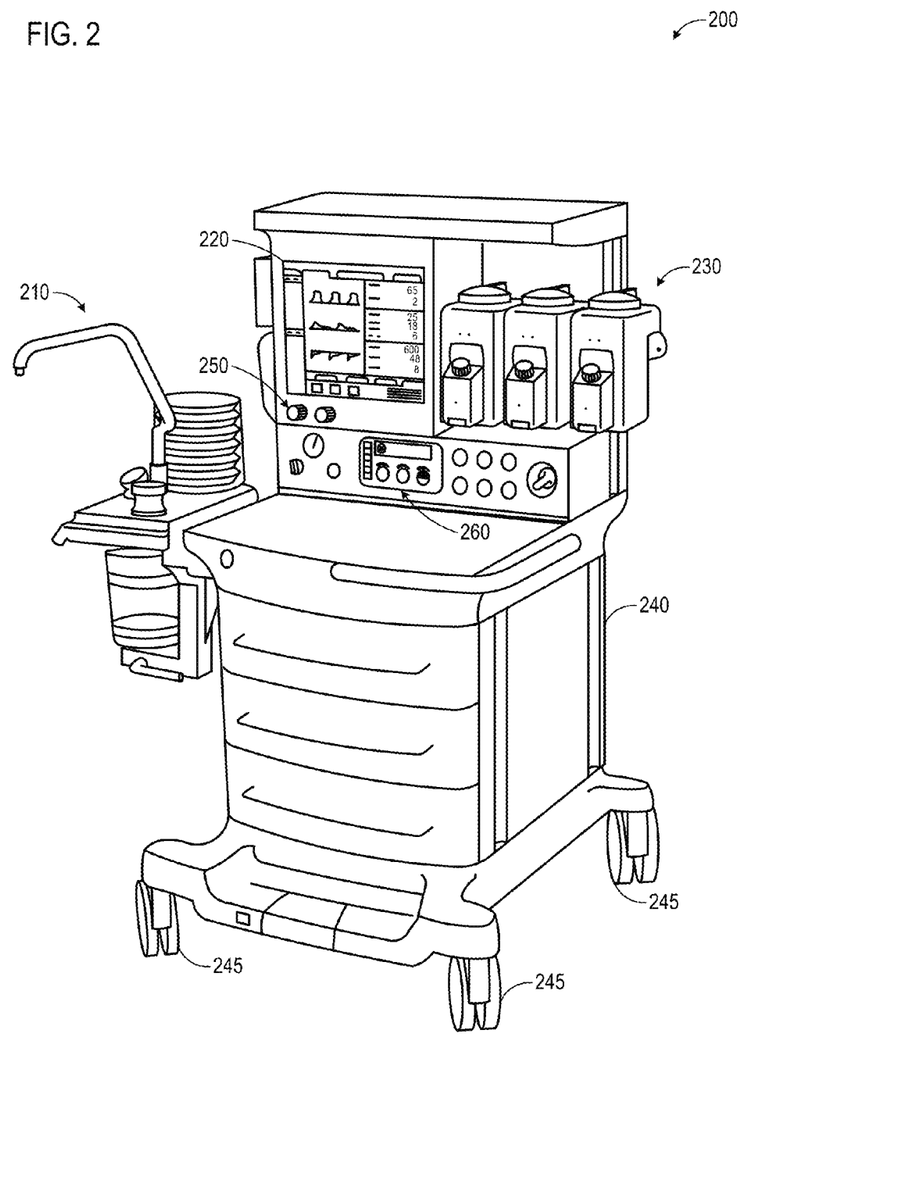
FIG. 2 illustrates an anesthesia delivery machine configured with two electronic flow selectors, configurable to selectively control each of the three gases, and three selectively deployable backup manual flow selectors, for controlling each of the three gases.

FIG. 2 illustrates an anesthesia delivery machine 200 configured with two electronic flow selectors 250, configurable to selectively control each of three gases, oxygen, nitrous oxide, and air. The anesthesia delivery machine 200 also includes three backup manual flow selectors 260, for controlling each of the three gases. The anesthesia delivery machine 200 may include a breathing system 210, anesthetic gas vaporizers 230, and/or other components of an anesthetic delivery system. The anesthesia delivery machine 200 may include a cart 240 and/or wheels 245 for portability. An electronic display 220 may provide information regarding the flow rate and/or anesthetic delivery process to a practitioner. Additionally, the electronic display 220 may be configured as a touch sensitive display to allow a practitioner to provide a selection of a flow rate.

The three backup manual flow selectors 260 may remain retracted and/or disabled when the anesthesia delivery machine 200 is in an electronic mode. When the anesthesia delivery machine 200 enters a manual mode (e.g., due to power loss or a user selection), the three backup manual flow selectors 260 may be deployed, unlocked, and/or otherwise functional. As previously described, various internals, switches, normally-open valves, normally-closed valves, three-way valves, and/or other components may regulate the flow of gases within the anesthesia delivery machine 200 based on whether it is in a manual mode or an electronic mode.

In an electronic mode, backup manual flow selectors 260 may be retracted, locked, disengaged, and/or otherwise non-operational. The flow rate of two or more gases may be controlled by the electronic flow selectors 250. The anesthesia delivery system may enter a manual mode due to the loss of power, in response to an electronic or a mechanical failure, and/or in response to a user selecting a manual mode.

Figure 3:
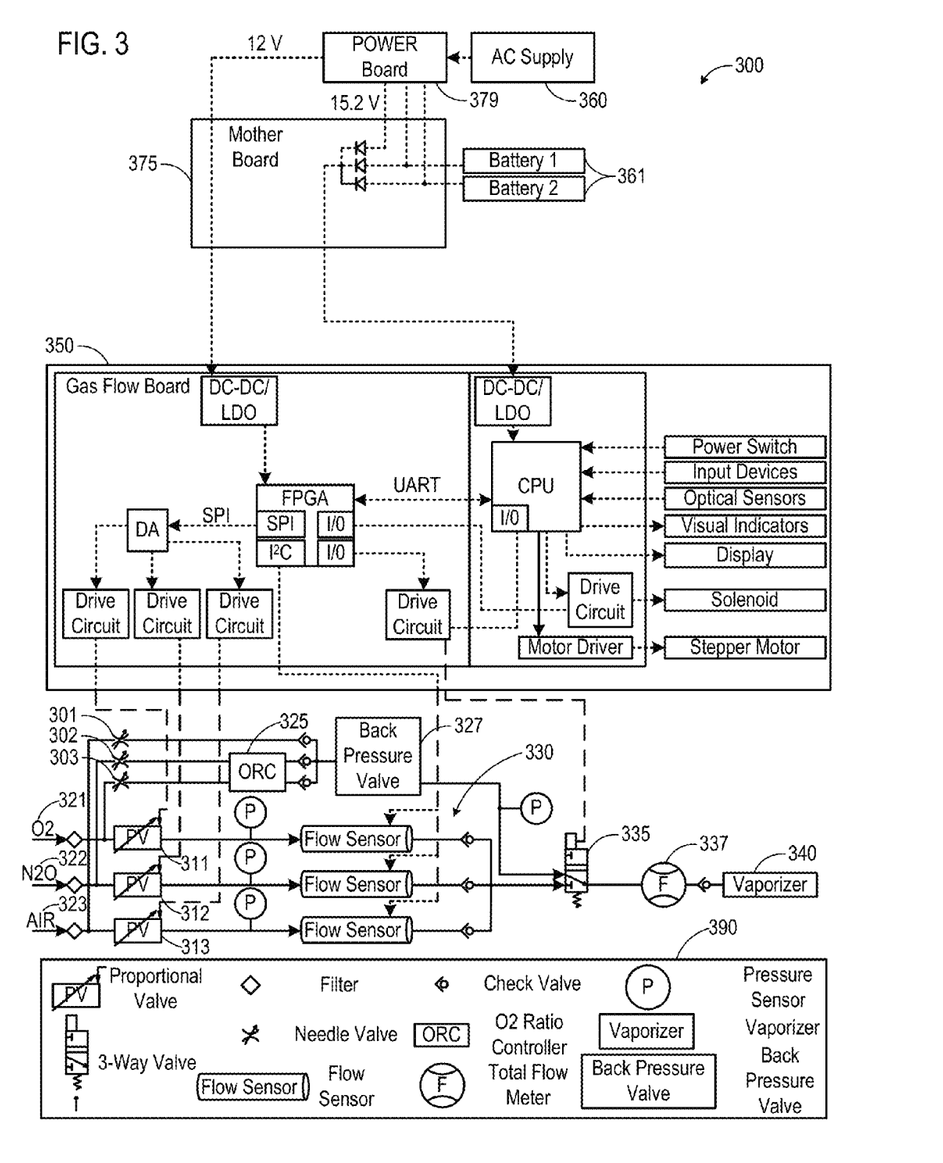
FIG. 3 illustrates a diagram of an anesthesia delivery system configured with electronic and backup manual controls for controlling the flow of oxygen, nitrous oxide, and air.

FIG. 3 illustrates a diagram 300 of an anesthesia delivery system configured with electronic flow control valves 311, 312, and 313 and backup mechanical flow control valves 301, 302, and 303 for controlling the flow of oxygen 321, nitrous oxide 322, and air 323. When power is available via AC supply 360 and/or batteries 361, the anesthesia delivery system may utilize electronic flow control valves 311, 312, and 313 controlled by one or more electronic flow selectors. The power input may be converted and/or inverted as necessary by a power board 379 and/or motherboard 375. A gas flow board 350 may include various monitoring and/or control components for electronically monitoring, regulating, and/or controlling the flow of gases within the anesthesia delivery system.

In various embodiments, the anesthesia delivery system may include various components and/or interface with various components via the gas flow board 350. For example, the gas flow board 350 may include and/or communicate with various FPGAs, CPUs, microprocessors, logic circuits, drive circuits, digital to analog converters, analog to digital converters, drive circuits, motor drivers, power switches, input devices, optical sensors, visual indicators, displays, solenoids, stepper motors, touch panels, and/or peripheral devices. Additionally, the gas flow board 350 may include and/or communicate with motor position switches, an LED, needle valve switches, a gas source, and/or other selection inputs. A practitioner may interact with the anesthesia delivery machine by providing inputs with regard to a flow of one or more gases. For instance, a practitioner may provide an input via an electronic flow selector. The electronic flow selector may comprise a mechanically rotatable knob and a rotary encoder.

When the anesthesia delivery system is in a powered state, the user may utilize an electronic mode or select a manual mode. When the anesthesia delivery system is in an unpowered state, the anesthesia delivery system may be used in a manual mode. In the electronic mode, the three source gases, oxygen 321, nitrous oxide, 322, and air 323, may flow through the electronic flow control valves 311, 312, and 313, an oxygen ratio controller 325, and/or check valves 330 and flow sensors. In a manual mode, the three source gases 321, 322, and 323 may flow through backup mechanical flow control valves 301, 302, and 303, oxygen ratio controller 325, and/or backpressure valve 327.

As described herein, a user may select a flow rate of a combination of oxygen and air to be supplied to a patient. A user may also select a flow rate of nitrous oxide to be provided to a patient instead of air. In some embodiments, the nitrous oxide may be supplied in addition to air. Regardless of the selections made by a user, a safe amount of oxygen may automatically be supplied to the patient, as ensured by the oxygen ratio controller (ORC) 325.

In various embodiments, a user may achieve a desired ratio of gases 321, 322, and 323 by starting with zero flow and sequentially adding source gases to the total flow, noting the effect of each on total flow rate. In an alternative embodiment, the user may achieve a desired ratio of gases 321, 322, and 323 by starting at a "home state" flow of oxygen 321 and then adjusting each of the gases 321, 322, and 323 to achieve the desired flow rate. The oxygen ratio controller 325 may ensure a clinically safe ratio of oxygen to nitrous oxide. The check valves 330 may prevent back flow of gases 321, 322, and 323 due to potential higher downstream pressures.

In either flow control mode, after passing through the check valves 330, the flows of the three gases 321, 322, and 323 may be combined into a single flow, which may be measured by a total flow meter, and pass through a total flow meter 337. An anesthetic gas vaporizer 340 may vaporize an anesthetic into the gases. A three-way selector valve 335 may be used to direct a flow of gases from only one of the backup mechanical flow control valves 301, 302, and 303 and the electronic flow control valves 311, 312, and 313. Alternatively, the three-way selector valve may comprise a one or more normally-open and/or normally-closed valves. Alternative diversion valve systems may be employed in place of a three-way selector valve 335 and/or normally-open and/or normally-closed valves.

In an electronic mode, flow control selectors associated with the backup mechanical flow control valves 301, 302, and 303 may be disabled, retracted, locked, and/or otherwise disengaged. In a manual mode (whether entered due to power loss or user selection), flow control selectors associated with the needle valves 301, 302, and 303 may be enabled, deployed, unlocked, and/or otherwise engaged. Various elements of the diagram 300 are illustrated in the key 390 and are not described in detail herein. Additionally, any of a wide variety of components, measurement devices, monitoring devices, and/or control devices configured for use in anesthesia delivery systems, gas delivery systems, liquid delivery systems, and/or other related systems may be added to, supplemented within, and/or replace components within the illustrated system.

Figure 4A:
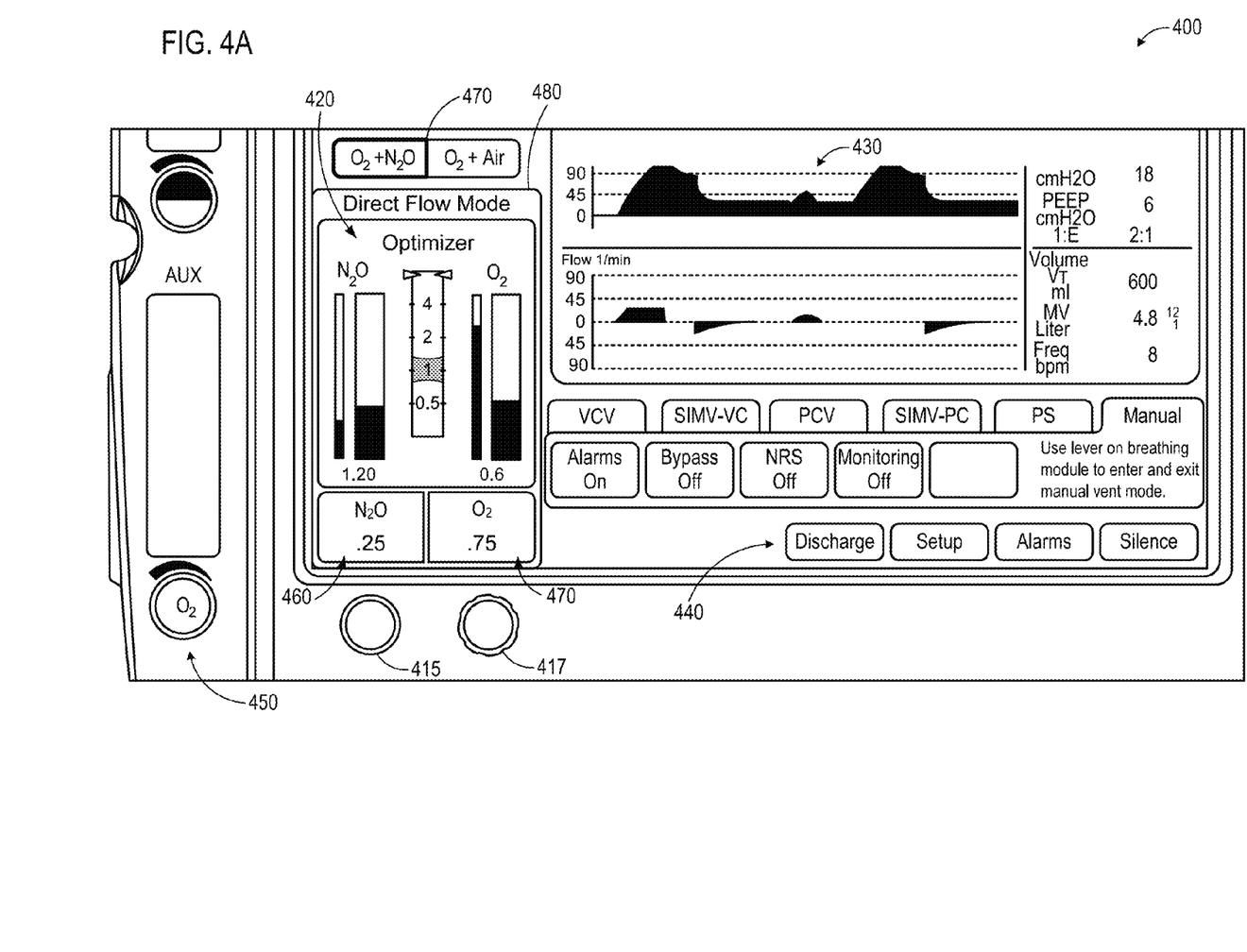
FIG. 4A illustrates a close-up view of a control panel of an anesthesia delivery machine, including two electronic flow selectors selectively configurable to directly control either oxygen and nitrous oxide or oxygen and air in a direct flow mode.

FIG. 4A illustrates a close-up view of a control panel 400 of an anesthesia delivery machine, including two electronic flow selectors 415 and 417 selectively configurable to directly control either oxygen and nitrous oxide or oxygen and air, at 470, in a direct flow mode, at 480. As illustrated, the anesthesia delivery machine may include a panel 430 to display various telemetry data associated with a patient, information associated with the flow rate of gases, and/or information associated with the delivery of one or more anesthetics. Various inputs 440 may be available to change the display of panel 430 and/or to control the anesthesia delivery machine.

In a first position, a selection toggle 470 may allow a practitioner to control the flow rate of oxygen and nitrous oxide via the respective electronic flow selectors 415 and 417. In a second position, the selection toggle 470 may allow a practitioner to control the flow rate of oxygen and air via the respective flow selectors 415 and 417. Depending on the position of the selection toggle 470, various flow rate monitoring devices and ratio measuring devices 420 may indicate the flow rate of one or more gases and/or a combination of gases. In various embodiments, auxiliary inputs and outputs 450 for oxygen and/or another gas may be available.

While the illustrated embodiment shows two electronic flow selectors 415 and 417, any number of flow selectors and associated gases may be utilized. For example, a flow control system may be configured to allow for the electronic and backup manual control of one, two, three, four . . . or N number of gases or liquids. In some embodiments, more than one flow selector (e.g., knob, toggle, dial, slider, switch) may be configured to control the flow rate of the same gas. An additional selection toggle 470 and/or a multi-position selection toggle may be used to control the number of gases controlled by any number of corresponding flow control selection knobs. The flow selectors may include and/or utilize any analog or digital selection mechanism for selecting a flow rate, including knobs as illustrated in the figures.

In the direct flow mode, at 480, a first flow selector 415 may be utilized to directly select the flow rate of either nitrous oxide or air, depending on which balance gas is selected via selection toggle 470. A second flow selector 417 may be utilized to directly select the flow rate of oxygen. As previously described, a rotary encoder associated with each of electronic flow selectors 415 and 417 may encode the selection. An electronic controller may then use the encoded selections to control the flow rate of the respective gases through an electronic flow control valve, such as an electronic proportional valve.

Numeric values 460 and 470 and associated graphical representations 420 may be displayed as a direct flow rate (e.g., liters per minute) or as a percentage flow rate for each controlled gas. Alternatively, the numeric values 460 and 470 and/or the graphical representations 420 may display the selected flow rates of each gas, a total flow rate, the ratio of the two gases, the total flow rate with respect to an optimum flow rate, and/or other numeric values, charts, graphs, percentages, and the like associated with the flow rates. In the illustrated embodiments, nitrous oxide is illustrated as representing one fourth (¼ or 0.25) of the total flow rate of the gases and oxygen is illustrated as representing three-fourths (¾ or 0.75) of the total flow rate of the gases.

Figure 4B:
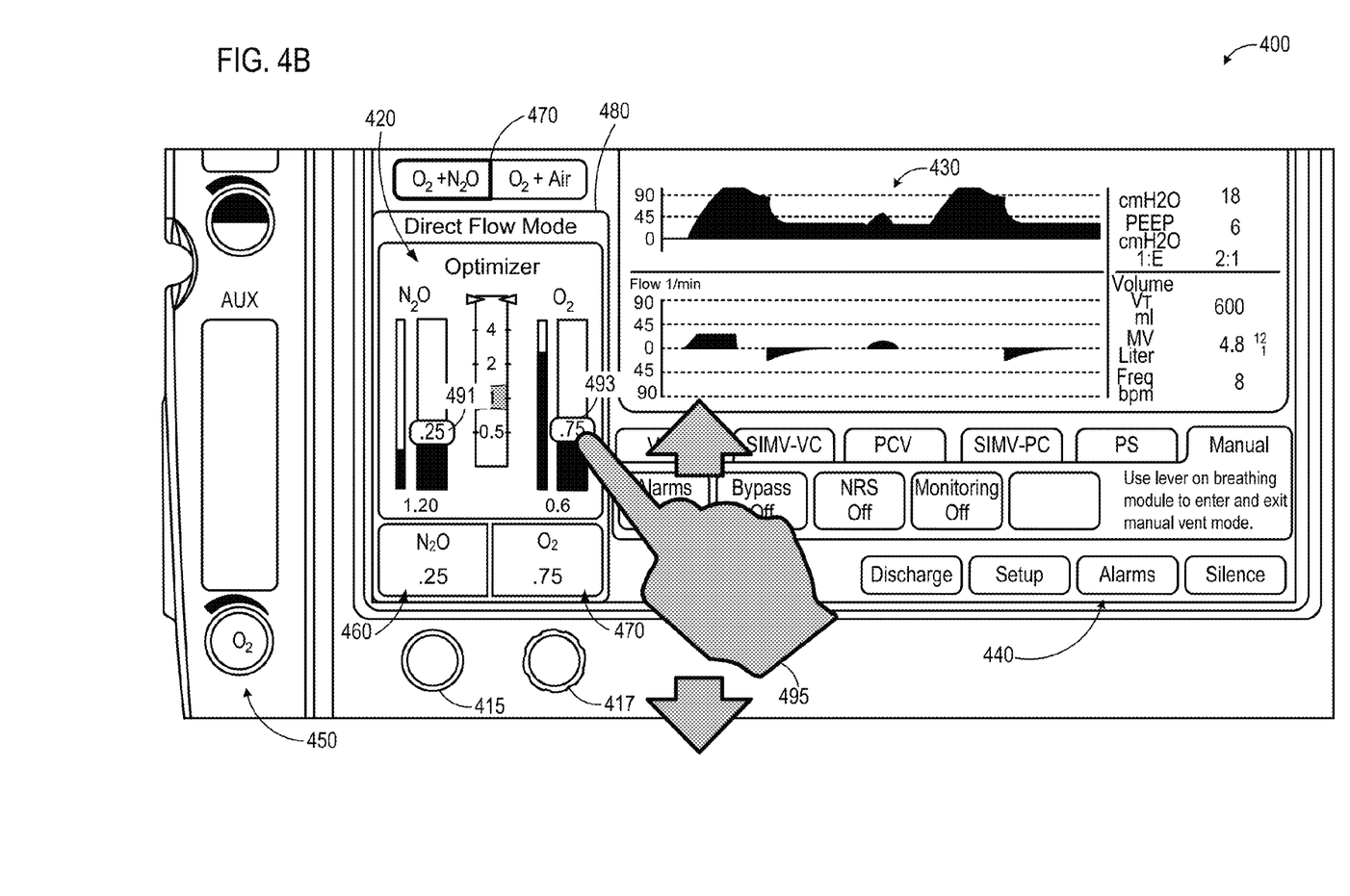
FIG. 4B illustrates the control panel of the anesthesia delivery machine, further including two electronic sliders configured to control the flow rate of the gases in the direct flow mode.

FIG. 4B illustrates the control panel 400 of the anesthesia delivery machine, further including two electronic sliders 491 and 493 configured to control the flow rate of the gases in the direct flow mode. As illustrated, in addition to the electronic flow selectors 415 and 417 and the other components described above, a user 495 may interact with a touch screen interface by sliding the electronic sliders 491 and 493 up or down.

In the direct flow mode, at 480, a first slider 491 may be utilized to directly select the flow rate of either nitrous oxide or air, depending on which balance gas is selected via selection toggle 470. A second slider 493 may be utilized to directly select the flow rate of oxygen. An electronic controller may then use the encoded selections to control the flow rate of the respective gases through an electronic flow control valve, such as an electronic proportional valve. The numeric values 460 and 470 and the touch icon numeric values in sliders 491 and 493 may be updated automatically when either of the electronic flow selectors 415 and 417 or the sliders 491 and 493 are used.

Figure 5A:
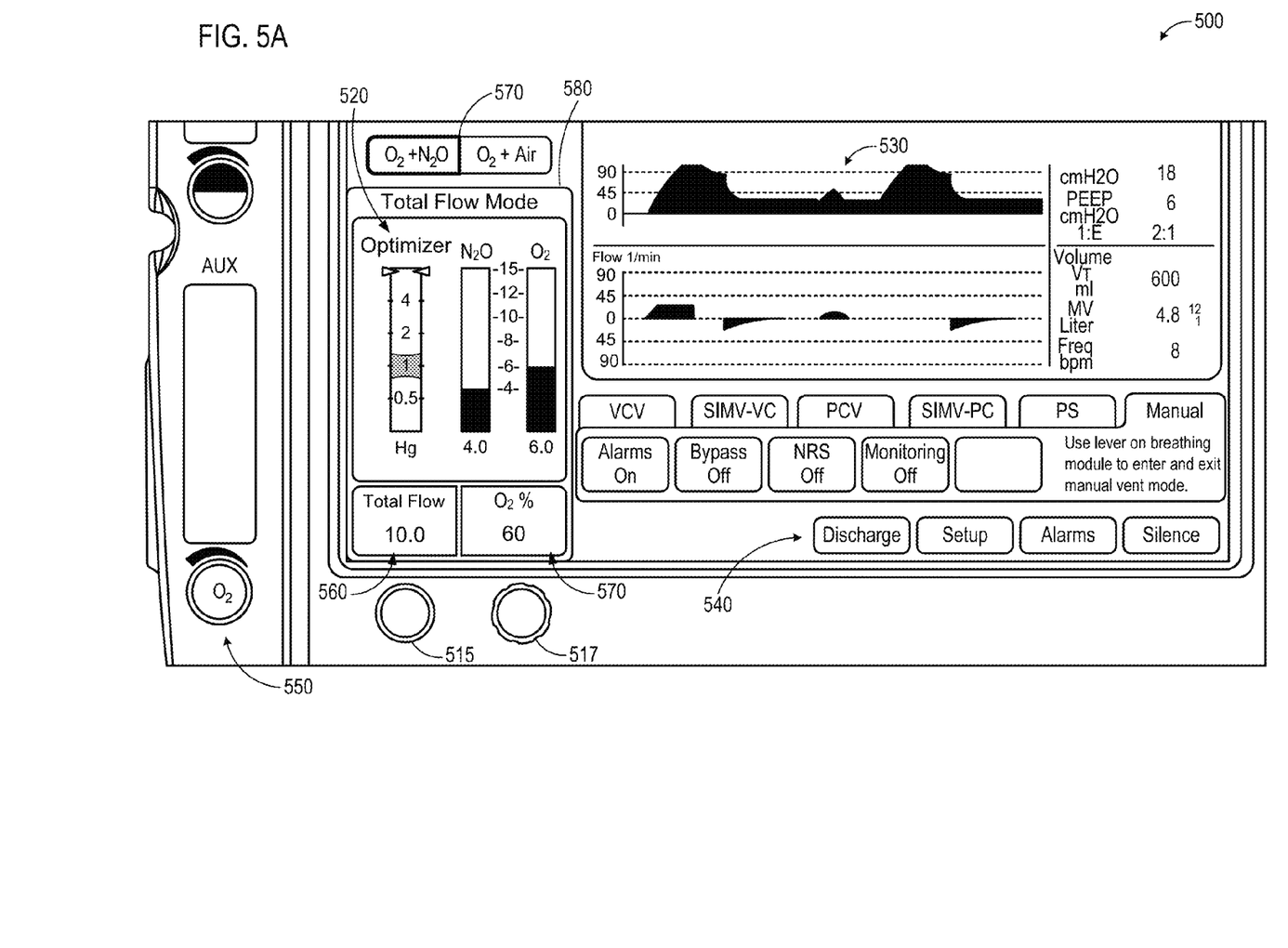
FIG. 5A illustrates a close-up view of a control panel of an anesthesia delivery machine, including two electronic flow selectors selectively configurable to control the ratio of oxygen to the total flow rate of oxygen combined with nitrous oxide or air.

FIG. 5A illustrates a close-up view of a control panel 500 of an anesthesia delivery machine, including two electronic flow selectors 515 and 517 selectively configurable to directly control either oxygen and nitrous oxide or oxygen and air, at 570, in a total flow mode, at 580. As illustrated, the anesthesia delivery machine may include a panel 530 to display various telemetry data associated with a patient, information associated with the flow rate of gases, and/or information associated with the delivery of one or more anesthetics. Various inputs 540 may be available to change the display of panel 530 and/or to control the anesthesia delivery machine.

In a first position, a selection toggle 570 may allow a practitioner to control the flow rate of oxygen and nitrous oxide via the respective electronic flow selectors 515 and 517. In a second position, the selection toggle 570 may allow a practitioner to control the flow rate of oxygen and air via the respective flow selectors 515 and 517. Depending on the position of the selection toggle 570, various flow rate monitoring devices and ratio measuring devices 520 may indicate the flow rate of one or more gases and/or a combination of gases. In various embodiments, auxiliary inputs and outputs 550 for oxygen and/or another gas may be available.

While the illustrated embodiment shows two electronic flow selectors 515 and 517, any number of flow selectors and associated gases may be utilized. For example, a flow control system may be configured to allow for the electronic and backup manual control of one, two, three, four . . . or N number of gases or liquids. In some embodiments, more than one flow selector (e.g., knob, toggle, dial, slider, switch) may be configured to control the flow rate of the same gas. An additional selection toggle 570 and/or a multi-position selection toggle may be used to control the number of gases controlled by any number of corresponding flow control selection knobs. The flow selectors may include and/or utilize any analog or digital selection mechanism for selecting a flow rate, including knobs as illustrated in the figures.

In the total flow mode, at 580, the first electronic flow selector 515 is used to adjust the total flow rate of the gases. That is, the first electronic flow selector 515 may be used to adjust the total flow rate of the selected balance gas (air or nitrous oxide) combined with the oxygen. The second electronic flow selector 517 may be used to control the concentration of oxygen to mix with the selected balance gas (air or nitrous oxide), depending on which balance gas is selected via selection toggle 570. The selections may be encoded by a rotary encoder and transmitted to an electronic controller. The ratio and necessary flow rates may be computed by the electronic controller. The electronic controller may then use the encoded selections to control the flow rate of the respective gases through an electronic flow control valve, such as an electronic proportional valve.

Numeric values 560 and 570 and associated graphical representations 520 may be displayed as a direct flow rate (e.g., liters per minute) or as a percentage flow rate for each controlled gas. Alternatively, the numeric values 560 and 570 and/or the graphical representations 520 may display the selected flow rates of each gas, a total flow rate, the ratio of the two gases, the total flow rate with respect to an optimum flow rate, and/or other numeric values, charts, graphs, percentages, and the like.

In the illustrated embodiments, nitrous oxide is illustrated as the selected balance gas, at 570. The first electronic flow selector 515 has been used to select a total flow rate of 10.0. The total flow rate may be unit-less, measured in liters per minute, kilograms per minute, and/or another volume or weight unit with respect to time. The second electronic flow selector 517 may be used to select the percentage of the oxygen (illustrated as 60 percent) in the total flow of gases.

Figure 5B:
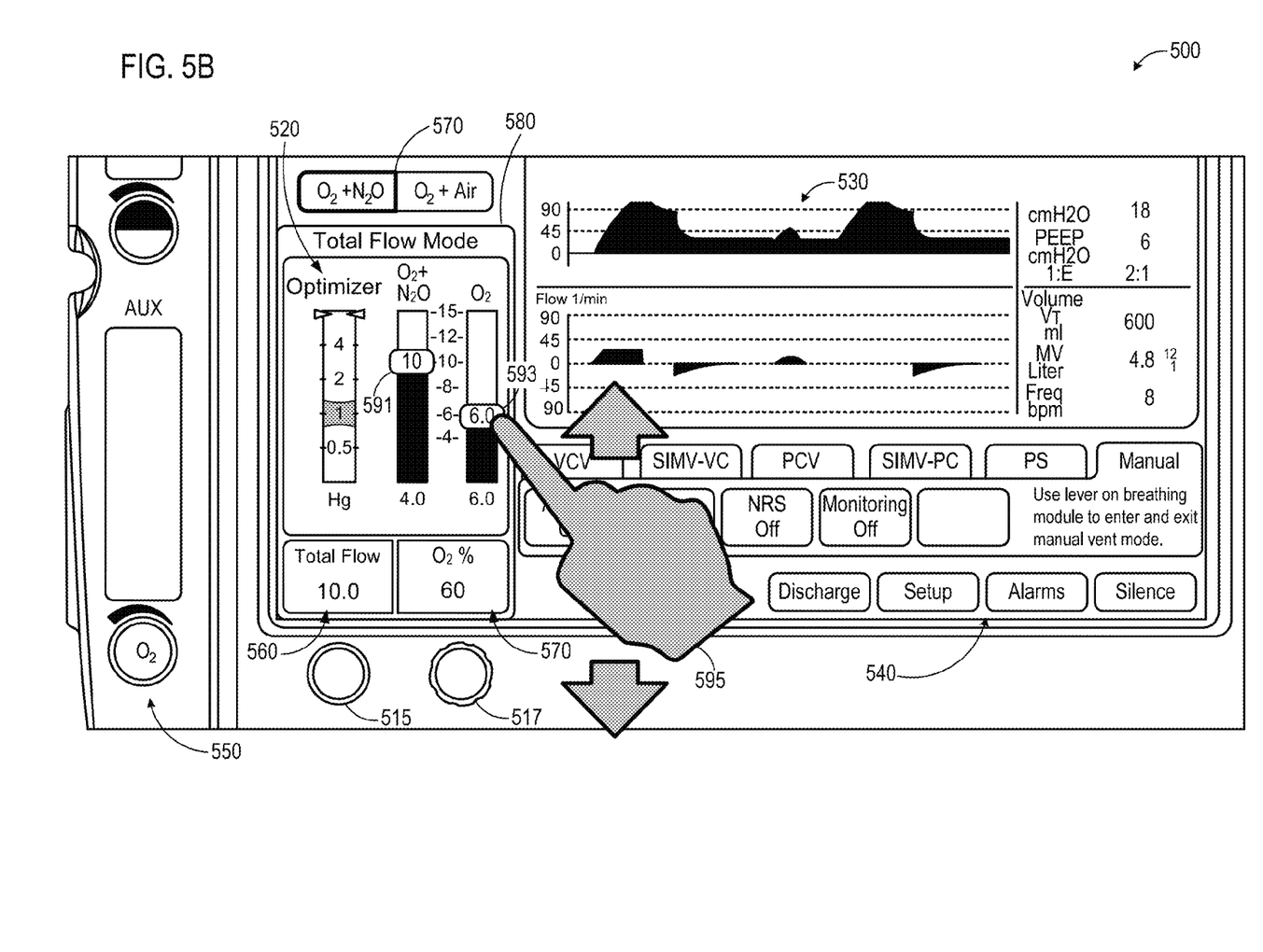
FIG. 5B illustrates the control panel of the anesthesia delivery machine, further including two electronic sliders configured to control the flow rate of the gases in the total flow mode.

FIG. 5B illustrates the control panel 500 he anesthesia delivery machine, further including two electronic sliders 591 and 593 configured to control the flow rate of the gases in the total flow mode. As illustrated, in addition to the electronic flow selectors 515 and 517 and the other components described above, a user 595 may interact with a touch screen interface by sliding the electronic sliders 591 and 593 up or down.

In the total flow mode, at 580, a first slider 591 may be utilized select the total flow rate of the selected balance gas and oxygen. A second slider 593 may be utilized to directly select the flow rate of oxygen. In the illustrated embodiment, the visual displays of the measuring device 520 may illustrate an optimizer, a total flow rate of the combined gases, and the flow rate of the oxygen. The numeric values 560 and 570 and the touch icon numeric values in sliders 591 and 593 may be updated automatically when either of the electronic flow selectors 515 and 517 or the sliders 591 and 593 are used. The ratio and necessary flow rates selected via the electronic flow selectors 515 and 517 and/or the sliders 591 and 593 may be computed by the electronic controller. The electronic controller may then use the encoded selections to control the flow rate of the respective gases through an electronic flow control valve, such as an electronic proportional valve.

Figure 6:
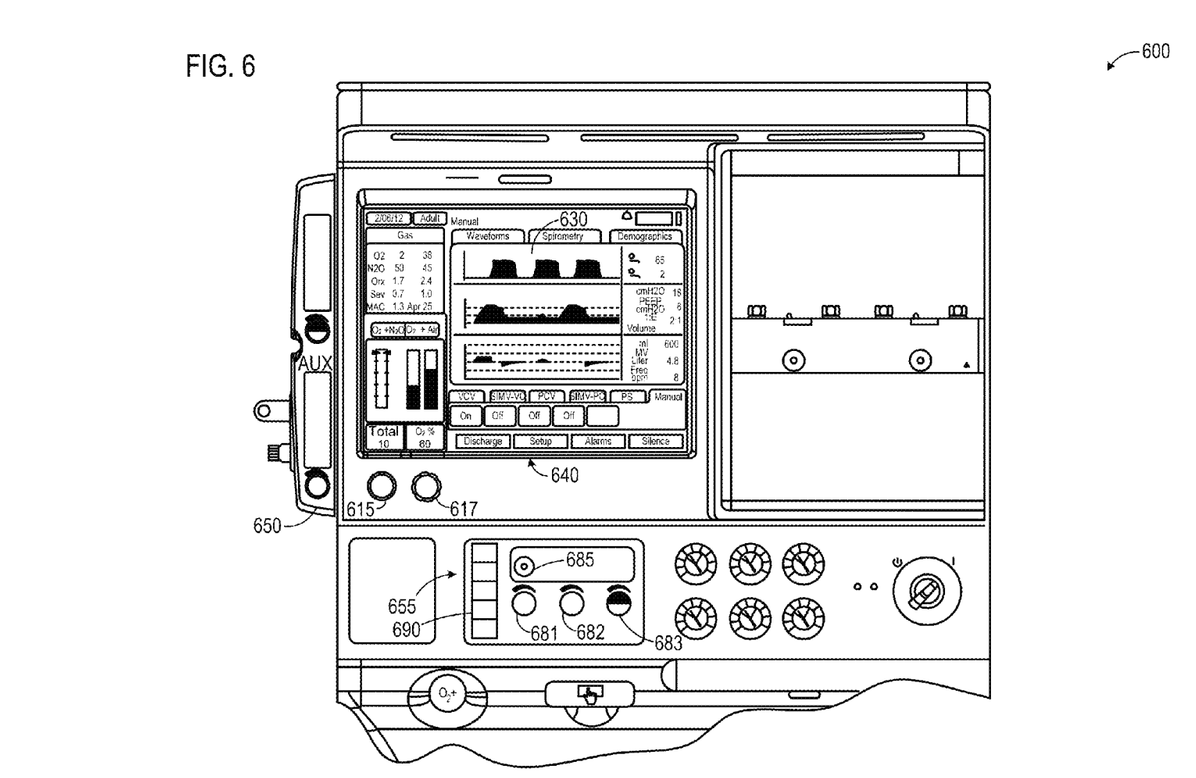
FIG. 6 illustrates a wider view of a control panel of an anesthesia delivery machine, including dual mode electronic flow selectors and backup mechanical flow controls for controlling the flow of three gases independently.

FIG. 6 illustrates a wider view of a control panel 600 of an anesthesia delivery machine, including dual mode electronic flow selectors 615 and 617 and backup mechanical flow controls 681, 682, and 683 for controlling the flow of three gases independently. When the anesthesia delivery system is in an electronic mode the two electronic flow control selectors 615 and 617 may be used to control either oxygen and nitrous oxide or oxygen and air, depending on the selection made via a selection toggle. An electronic display 630 may display information associated with the flow rate of one or more gases, an anesthetic, and/or patient telemetry data. Various touch inputs 640 may be available. An auxiliary control panel 650 may allow for one or more gases to be supplied to an auxiliary device.

A mode selector may be used to select either a direct flow control mode or a total flow control mode. In a direct flow mode, a first electronic flow selector may be used to directly adjust the flow rate of either nitrous oxide or air, depending on the selected balance gas. A second electronic flow selector may be used to directly adjust the flow rate of oxygen. A digital display associated with the selected flow rates may display the selected flow rates of each gas, a total flow rate, the ratio of the two gases, the total flow rate with respect to an optimum flow rate, and/or other numeric values, charts, graphs, percentages, and the like.

The same system may be selectively used in a total flow mode. In a total flow mode, a first electronic flow selector may be used to adjust the total flow rate of the gases, including the selected balance gas (air or nitrous oxide) and the oxygen. A second electronic flow selector may be used to control the concentration of oxygen to mix with the selected balance gas (air or nitrous oxide). The selections may be encoded by one or more rotary encoders and transmitted to an electronic controller. The ratio and necessary flow rates may be computed by the electronic controller. The electronic controller may then use the encoded selections to control the flow rate of the respective gases through an electronic flow control valve, such as an electronic proportional valve.

Numeric values and associated graphical representations may be displayed as a direct flow rate (e.g., liters per minute) or as a percentage flow rate for each controlled gas. Alternatively, the numeric values and/or the graphical representations may display the selected flow rates of each gas, a total flow rate, the ratio of the two gases, the total flow rate with respect to an optimum flow rate, and/or other numeric values, charts, graphs, percentages, and the like.

When the anesthesia delivery system is in an unpowered state and/or the user has selected a manual mode, the anesthesia delivery system may be in a manual mode. In a manual mode, the flow rate of one or more gases and/or the amount of anesthetic delivery may be controlled via a manual panel 655. The electronic display 630, the touch inputs 640, the electronic flow control selectors 615 and 617, and other electronic components may be unavailable in an unpowered state and one or more of them may be unavailable and/or otherwise disabled in a manual mode selected when in a powered state.

The manual panel 655 may include a total flow rate indicator 690, a manual mode selector 685 (e.g., a spring-loaded plunger), and one or more manually operated flow control selectors 681, 682, and 683. According to various embodiments, a manually operated flow control selector may be available for each available gas or for each available critical gas. In various embodiments, manually operated flow control selectors 681, 682, and 683 may be disabled, retracted, locked, and/or otherwise not operational when the anesthesia delivery system is in an electronic mode. In a manual mode, the manually operated flow control selectors 681, 682, and 683 may be enabled, deployed, unlocked, and/or otherwise become operational.

A gas flow control system, according to any of the various embodiments described herein, may be used in conjunction with any of a wide variety of applications. In the illustrated embodiments, the gas flow control systems are shown as parts of anesthesia delivery systems. In such embodiments, the combined flow of one or more gases may be injected or otherwise infused with anesthesia, such as via a vaporizer, for a controlled delivery of the anesthesia and/or the one or more gases to a patient.

This disclosure has been made with reference to various exemplary embodiments, including the best mode. However, those skilled in the art will recognize that changes and modifications may be made to the exemplary embodiments without departing from the scope of the present disclosure. While the principles of this disclosure have been shown in various embodiments, many modifications of structure, arrangements, proportions, elements, materials, and components may be adapted for a specific environment and/or operating requirements without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. The scope of the present invention should, therefore, be determined by the following claims.

What is claimed is:

1. A fluid flow control system for controlling the flow rate of a fluid, comprising:
    a programmable controller;
    a first electronic flow control valve configured to selectively control the flow rate of a first fluid based on a control signal from the programmable controller;
    a second electronic flow control valve configured to selectively control the flow rate of a second fluid based on a second control signal from the programmable controller;
    a first rotatable flow selector configured for dual use in both a total flow control mode and a direct flow control mode and configured to allow a user to select a relative flow rate of at least the first fluid;
    a second rotatable flow selector configured for dual use in both a total flow control mode and a direct flow control mode and configured to allow a user to select a relative flow rate of the second fluid,
    a first rotary encoder in communication with the programmable controller, the first rotary encoder configured to electronically encode the selection made via the first flow selector and configured for dual use in both the total flow control mode and the direct flow control mode;
    a second rotary encoder in communication with the programmable controller, the second rotary encoder configured to electronically encode the selection made via the second flow selector and configured for dual use in both the total flow control mode and the direct flow control mode; and
    a mode selector in communication with the programmable controller, the mode selector configured to allow for the selection of either the direct flow control mode or the total flow control mode,
    wherein the programmable controller is configured to transmit control signals to each of the first and second electronic flow control valves to control the flow rate of the first and second fluids, based on:
        the electronically encoded selections from the first and second rotary encoders; and
        the selection of either the total flow control mode or the direct flow control mode,
        wherein in the total flow control mode, the first rotatable flow selector is configured to allow for the selection of a total flow rate of a combination of the first and second fluids independent of an adjustment to a ratio of the flow rates of the first and second fluids, and
        wherein in the total flow control mode, a change in the flow rate of the second fluid via the second rotatable flow selector changes a ratio of the second fluid to the first fluid without significantly changing the total flow rate of the first and second fluids due to an automatic and corresponding change in the flow rate of the first fluid.

2. The fluid flow control system of claim 1, wherein the second fluid comprises oxygen.

3. The fluid flow control system of claim 1, wherein the first fluid comprises one of nitrous oxide and air.

4. The fluid flow control system of claim 1, further comprising an electronic balance gas selector configured to allow for the selection of the first fluid as one of nitrous oxide and air.

5. The fluid flow control system of claim 1, wherein each of the first and second electronic flow control valves comprises an electronic proportional valve.

6. The fluid flow control system of claim 1, wherein each of the first and second rotatable flow selectors comprises a rotatable knob.

7. The fluid flow control system of claim 1, further comprising a vaporizer configured to inject an anesthetic into at least one of the first and second fluids.

8. The fluid flow control system of claim 1, further comprising an electronic display that, when in the total flow control mode, is configured to display a first numeric value corresponding to the total flow rate of the first and second fluids and a second numeric value corresponding to the ratio of the flow rate of the second fluid to the total flow rate displayed as a percentage.

9. The fluid flow control system of claim 1, further comprising an electronic display that, when in the direct flow control mode, is configured to display a first numeric value corresponding to the flow rate of the first fluid and a second numeric value corresponding to the flow rate of the second fluid.

10. The fluid flow control system of claim 1, further comprising an electronic display configured to display a virtual flow tube with a simulated float within a variable area flowmeter corresponding to a flow rate of one of the first and second fluids.

11. A fluid flow control system for controlling the flow rate of a fluid, comprising:
    a programmable controller;
    a first electronic flow control valve configured to selectively control the flow rate of a first fluid based on a control signal from the programmable controller;
    a second electronic flow control valve configured to selectively control the flow rate of a second fluid based on a second control signal from the programmable controller;
    a first, dual-use rotatable flow selector configured to allow for the selection of a flow rate of a first fluid in a direct flow control mode and a total flow rate of the first and second fluids via the first and second electronic flow control valves, respectively, in a total flow control mode;
    a second, dual-use rotatable flow selector configured to allow for the selection of a flow rate of the second fluid via the second electronic flow control valve in both a direct flow control mode and a total flow control mode,
    wherein, in the total flow control mode, an increase in the flow rate of the second fluid via the second rotatable flow selector changes a ratio of the second fluid to the first fluid without significantly changing the total flow rate of the first and second fluids due to an automatic and corresponding decrease in the flow rate of the first fluid;
    a first rotary encoder in communication with the programmable controller configured to electronically encode the selection made via the first flow selector, regardless of whether the direct flow control mode or total flow control mode is selected;
    a second rotary encoder in communication with the programmable controller configured to electronically encode the selection made via the second flow selector, regardless of whether the direct flow control mode or total flow control mode is selected; and
    wherein, in the total flow control mode, the programmable controller is configured to transmit control signals to each of the first and second electronic flow control valves to control the flow rate of the first and second fluids, respectively, such that the total flow rate of the first and second fluids corresponds to the electronically encoded selection made via the first flow selector and the flow rate of the second fluid corresponds to the electronically encoded selection made via the second flow selector.

12. The fluid flow control system of claim 11, wherein the selection of the flow rate of the second fluid comprises a selection of a ratio of the flow rate of the second fluid relative to the total flow rate of the first and second fluids.

13. The fluid flow control system of claim 11, wherein the second fluid comprises oxygen.

14. The fluid flow control system of claim 11, wherein the first fluid comprises one of nitrous oxide and air.

15. The fluid flow control system of claim 11, further comprising an electronic balance gas selector configured to allow for the selection of the first fluid as one of nitrous oxide and air.

16. The fluid flow control system of claim 11, wherein each of the first and second electronic flow control valves comprises an electronic proportional valve.

17. The fluid flow control system of claim 11, wherein each of the first and second rotatable flow selectors comprises a rotatable knob.

18. The fluid flow control system of claim 11, further comprising a vaporizer configured to inject an anesthetic into at least one of the first and second fluids.

19. The fluid flow control system of claim 11, further comprising an electronic display configured to display a first numeric value corresponding to the total flow rate of the first and second fluids and a second numeric value corresponding to the ratio of the flow rate of the second fluid to the total flow rate displayed as a percentage.

20. The fluid flow control system of claim 11, further comprising an electronic display configured to display the total flow rate of the first and second fluids as a first numeric value and the flow rate of the second fluid as a second numeric value.

21. The fluid flow control system of claim 11, further comprising an electronic display configured to display a virtual flow tube with a simulated float within a variable area flowmeter corresponding to a flow rate of one of the first and second fluids.

22. A fluid flow control system for controlling the flow rate of a fluid, comprising:
a programmable controller;
a first electronic flow control valve configured to selectively control the flow rate of a first fluid based on a control signal from the programmable controller;
a second electronic flow control valve configured to selectively control the flow rate of a second fluid based on a second control signal from the programmable controller;
a first, dual-use rotatable flow selector configured to allow for the selection of a flow rate of a first fluid in a direct flow control mode and a total flow rate of the first and second fluids in a total flow control mode;
a second, dual-use rotatable flow selector configured to allow for the selection of a relative flow rate of the second fluid via the second electronic flow control valve in both a direct flow control mode and a total flow control mode,
wherein, in the total flow control mode, an increase in the flow rate of the second fluid via the second rotatable flow selector changes a ratio of the second fluid to the first fluid without a corresponding change to the total flow rate of the first and second fluids due to an automatic and corresponding decrease in the flow rate of the first fluid based on the selection of a total flow rate of the first and second fluids made via the first rotatable flow selector;
a first rotary encoder in communication with the programmable controller configured to electronically encode the selection made via the first flow selector independent of whether the direct flow control mode or total flow control mode is selected;
a second rotary encoder in communication with the programmable controller configured to electronically encode the selection made via the second flow selector independent of whether the direct flow control mode or total flow control mode is selected; and
wherein, in the total flow control mode, the programmable controller is configured to transmit control signals to each of the first and second electronic flow control valves to control the flow rate of the first and second fluids, respectively, based on the electronically encoded selections from the first and second rotary encoders.

23. The fluid flow control system of claim 22, further comprising an electronic display configured to display a virtual flow tube with a simulated float within a variable area flowmeter corresponding to the flow rate of one of the first and second fluids.

24. The fluid flow control system of claim 22, further comprising an electronic balance gas selector configured to allow for the selection of the first fluid as one of nitrous oxide and air.

25. The fluid flow control system of claim 22, further comprising an electronic display configured to display a first numeric value corresponding to the flow rate of the first fluid and a second numeric value corresponding to the flow rate of the second fluid.

26. The fluid flow control system of claim 22, wherein the second fluid comprises oxygen.

27. The fluid flow control system of claim 22, wherein the first fluid comprises one of nitrous oxide and air.

28. The fluid flow control system of claim 22, wherein each of the first and second electronic flow control valves comprises an electronic proportional valve.

29. The fluid flow control system of claim 22, wherein each of the first and second rotatable flow selectors comprises a rotatable knob.

30. The fluid flow control system of claim 22, further comprising a vaporizer configured to inject an anesthetic into at least one of the first and second fluids.

31. The fluid flow control system of claim 22, further comprising:
a third electronic flow control valve configured to selectively control the flow rate of a third fluid;
a third rotatable flow selector configured to allow for the selection of the flow rate of the third fluid via the third electronic flow control valve; and
a third rotary encoder configured to electronically encode the selection made via the third flow selector,
wherein the total flow rate is set by the first rotatable flow selector independent of the flow rate of the second and third fluids selected via the second and third rotatable flow selectors, respectively, and
wherein the controller is further configured to transmit a control signal to the third flow control valve to control the flow rate of the third fluid based on the electronically encoded selection from the third rotary encoder.

* * * * *